US009604018B2

(12) United States Patent
Gallem et al.

(10) Patent No.: US 9,604,018 B2
(45) Date of Patent: Mar. 28, 2017

(54) AEROSOL THERAPY DEVICE

(75) Inventors: Thomas Gallem, Munich (DE); Uwe Hetzer, Munich (DE); Mihaela Loenner, Poing (DE)

(73) Assignee: PARI Pharma GmbH, Starnberg (DE)

( * ) Notice: Subject to any disclaimer, the term of this patent is extended or adjusted under 35 U.S.C. 154(b) by 1255 days.

(21) Appl. No.: 13/133,517

(22) PCT Filed: Dec. 8, 2009

(86) PCT No.: PCT/EP2009/066599
§ 371 (c)(1),
(2), (4) Date: Oct. 25, 2011

(87) PCT Pub. No.: WO2010/066714
PCT Pub. Date: Jun. 17, 2010

(65) Prior Publication Data
US 2012/0037154 A1 Feb. 16, 2012

(30) Foreign Application Priority Data

Dec. 9, 2008 (DE) ........................ 10 2008 054 431

(51) Int. Cl.
*A61M 15/00* (2006.01)
(52) U.S. Cl.
CPC .... *A61M 15/0085* (2013.01); *A61M 15/0015* (2014.02); *A61M 15/0018* (2014.02); *A61M 15/0021* (2014.02)
(58) Field of Classification Search
CPC .. A61M 11/00; A61M 11/001; A61M 11/002; A61M 11/003; A61M 11/005;
(Continued)

(56) References Cited

U.S. PATENT DOCUMENTS 5,161,524 A * 11/1992 Evans ...................... 128/203.15
5,226,411 A * 7/1993 Levine .............. A61M 16/1085
128/203.26
(Continued)

FOREIGN PATENT DOCUMENTS

DE 19953317 C1 2/2001
DE 10126807 A1 12/2002
(Continued)

OTHER PUBLICATIONS

Bennett, W. D., "Controlled inhalation of aerosolised therapeutics", Expert Opinion Drug Delivery, 2005, 2(4):763-767, Ashley Publications.

(Continued)

*Primary Examiner* — Rachel Young
(74) *Attorney, Agent, or Firm* — Wolf, Greenfield & Sacks, P.C.

(57) ABSTRACT

The disclosure relates to an aerosol therapy device including: a housing; an aerosol generator, which is arranged in the housing; an air inlet, which is formed in the housing upstream of the aerosol generator; and an air outlet, which is formed in the housing downstream of the aerosol generator to administer the aerosol produced, wherein an air flow from the air inlet to the air outlet can be generated by a negative pressure at the air outlet, wherein the air flow flows around the aerosol generator, wherein a truncated-cone-shaped flow channel, the central axis of which extends in a curved manner, is arranged between the aerosol generator and the air outlet.

34 Claims, 4 Drawing Sheets

(58) Field of Classification Search
CPC .... A61M 11/006; A61M 11/02; A61M 11/04; A61M 11/041; A61M 11/042; A61M 15/00; A61M 15/001; A61M 15/0013; A61M 15/0015; A61M 15/0018; A61M 15/002; A61M 15/0021; A61M 15/0085; A61M 15/0086; A61M 15/0088; A61M 15/009; A61M 15/0091; A61M 15/0095
See application file for complete search history.

(56) References Cited

U.S. PATENT DOCUMENTS

| | | | |
|---|---|---|---|
| 5,518,179 A | | 5/1996 | Humberstone et al. |
| 5,584,285 A | | 12/1996 | Salter et al. |
| 5,692,492 A | * | 12/1997 | Bruna et al. ............. 128/200.23 |
| 6,571,790 B1 | * | 6/2003 | Weinstein ............... A61F 17/00 128/200.14 |
| 6,962,151 B1 | | 11/2005 | Knoch et al. |
| 7,131,440 B2 | | 11/2006 | Sonntag |
| 2001/0013341 A1 | | 8/2001 | Gallem |
| 2002/0056448 A1 | * | 5/2002 | Stapleton et al. ....... 128/200.14 |
| 2006/0207591 A1 | * | 9/2006 | Gallem ................ A61M 11/005 128/200.14 |
| 2007/0044792 A1 | * | 3/2007 | Ivri .................... B05B 17/0646 128/200.14 |
| 2008/0078383 A1 | * | 4/2008 | Richards et al. ........ 128/203.12 |
| 2008/0110453 A1 | * | 5/2008 | Ross et al. ............... 128/200.16 |
| 2008/0299049 A1 | * | 12/2008 | Stangl .............................. 424/45 |
| 2008/0308096 A1 | | 12/2008 | Borgschulte et al. |
| 2009/0293868 A1 | | 12/2009 | Hetzer et al. |

FOREIGN PATENT DOCUMENTS

| | | |
|---|---|---|
| DE | 10 2005 006374 B3 | 7/2006 |
| DE | 10 2005 038619 A1 | 2/2007 |
| EP | 0895788 A1 | 2/1999 |
| WO | WO 00/12161 A1 | 3/2000 |
| WO | WO 03/022332 A2 | 3/2003 |
| WO | WO 2006/078900 A1 | 7/2006 |

OTHER PUBLICATIONS

Brand, P. et al., "Total Deposition of Therapeutic Particles During Spontaneous and Controlled Inhalations", Journal of Pharmaceutical Sciences, vol. 89, No. 6, Jun. 2000, pp. 724-731.
English Translation of the International Preliminary Report on Patentability mailed Jun. 23, 2011 for International Application No. PCT/EP2009/066599.

* cited by examiner

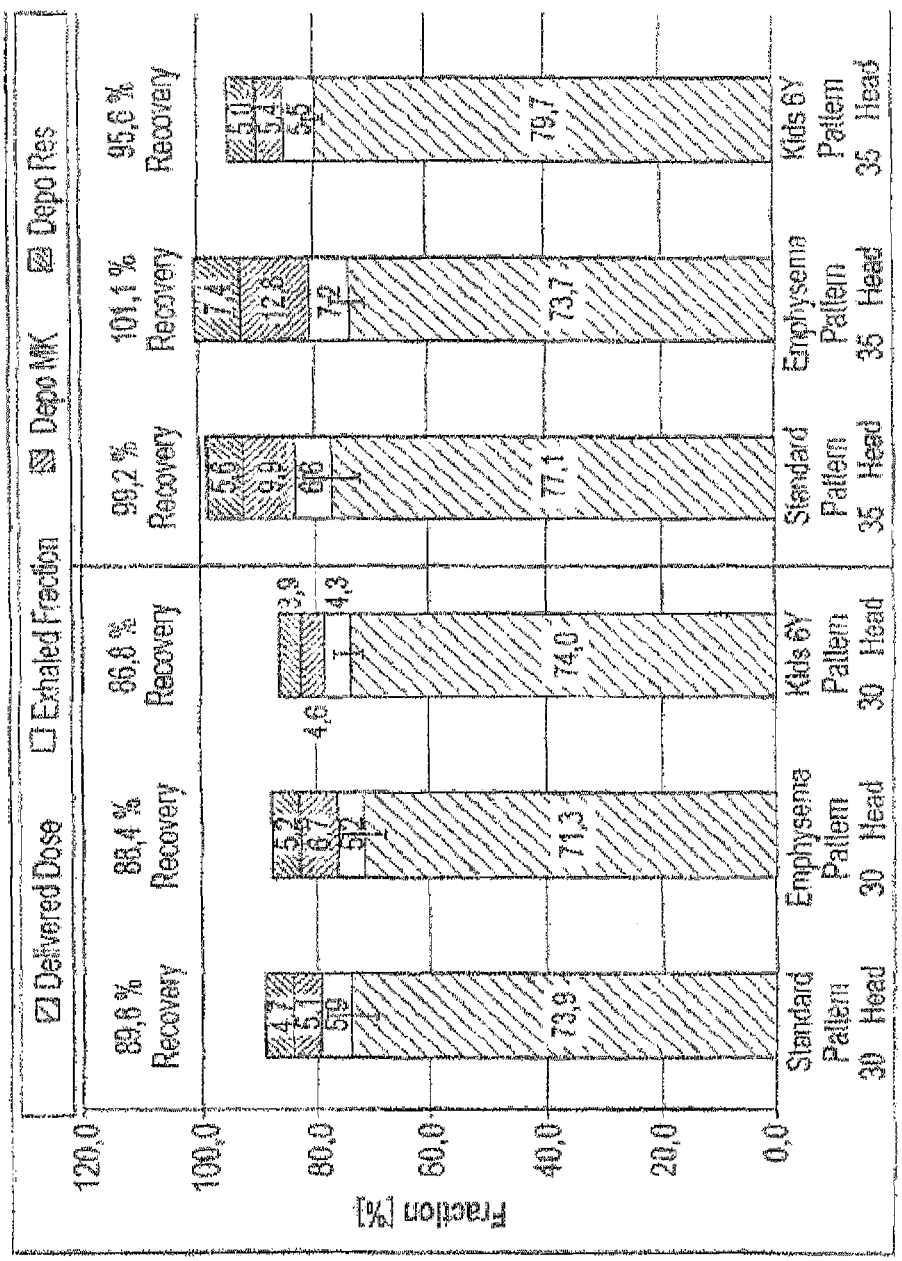

AEROSOL THERAPY DEVICE

The present invention relates to an aerosol therapy device having the features of the preamble of claim 1.

Such an aerosol therapy device is known, for example, from DE 199 53 317 C2 or DE 10 2005 038 619 A1. In such devices, therapeutically effective or medicament-containing liquids are nebulised by means of an aerosol generator into an aerosol that regularly consists of respirable particles. The aerosol is offered to a patient for inhalation within the scope of a therapy, whereby the therapeutically effective liquid or the medicament enters the respiratory tract of the patient. For this purpose, a flow of air from an air inlet of a housing of the aerosol therapy device to an air outlet is generated upon inhalation by the patient, said airflow bypassing (flowing around) the aerosol generator and taking with it the aerosol which is formed by the aerosol generator and is to be administered. Upon exhalation, the exhaled air is preferably expelled from the housing to the fullest possible extent via a non-return valve in the region of the air outlet, without thereby adversely affecting the process of continuous aerosol generation or of mixing the aerosol. The breathing manoeuvres (inhalation and exhalation) can differ greatly from patient to patient. In addition to an average healthy adult, the aerosol therapy devices are also used, inter alia, by children. However, the breathing manoeuvre of an average healthy child differs in many respects, for example in the number of breaths per minute, the respiratory volumes or the ratio between the length of inhalation and the length of exhalation. An adult patient with emphysema, whose average number of breaths per minute lies somewhere between that of a healthy child and that of a healthy adult, can also be cited as a further example of a possible user of the aerosol therapy device. The respiratory volumes as well as the ratio between the length of inhalation and the length of exhalation also differ from one another in this case.

As a result, if the aerosol therapy devices are used by different patients or users, a different time profile of the airflow (flow velocity, flow rate, etc) through the device is generated. However, it is highly important in particular when administering a medicament to be able to administer a predetermined constant dose. In other words, it is necessary that an amount of nebulised medicament which corresponds to the desired dose is provided at the air outlet of the device. However, in the case of different respiratory patterns through the device, there is the danger that different amounts will arrive at the air outlet depending on the airflow over time and thus that the desired dosage accuracy cannot be achieved.

This is particularly important for users in whom a deterioration of the condition of the lungs and thus an alteration of the inhalation manoeuvre occurs from one inhalation to the next. This can happen repeatedly in patients with lung disease, owing, for example, to exacerbations over the course of the illness. In spite of or precisely during these deteriorations, the user (patient) should receive a constant and equivalent medicament dosage, and this should occur irrespective of the point of inhalation and of the possible inhalation manoeuvre.

The object of the present invention is to create an aerosol therapy device which enables a substantially constant release of aerosol at the air outlet, i.e. within a predetermined range, basically irrespective of the user (patient) as well as their disease state, and thus of the generated respiratory pattern.

This object is solved by the features of claim 1. Advantageous further developments of the present invention can be found in the sub-claims.

The idea forming the basis for the present invention is to design the flow channel between the aerosol generator and the air outlet in such a manner that a flow of air or aerosol from the aerosol generator to the air outlet which is as laminar as possible can be achieved. Owing to this flow-optimised air guidance, deposits of the aerosol on the inner walls of the housing of the aerosol therapy device can be significantly reduced or can be as good as avoided. Contributing to this is also the fact that the inhaled air bypasses the aerosol generator in the form of an "enveloping flow" such that as little turbulence as possible occurs in the direct vicinity of the aerosol generator, as a result of which a higher deposition rate that is associated therewith can be avoided.

The deposition of the medicament in the lungs and thus a successful inhalation therapy substantially depends on the droplet size distribution and the aerosol output rate as well as on the respiratory pattern of the patient. The medicament aerosol has different characteristics and modes of action in the body. The inhalation device influences the aerosol size (MMD, MMAD), distribution (GSD) and output rate (TOR) of the respective liquid medicament. The structure and state (morphometry) of the patient's lungs also have a significant influence on the deposition in the lungs and the success of therapy.

This can be best explained using an example. An effective medicament paired with a poor nebuliser (aerosol generator) will lead to a medicament aerosol having a larger MMD. Aerosol droplets which are too large will be generated. These cannot pass through the larynx, vocal chords and the first bifurcations of the respiratory tract during inhalation. Thus, during corticoid inhalation, for example, increased deposition of the medicament aerosol can occur in these areas, which can lead to fungal infections in the mouth (thrush). The breathing manoeuvre also affects inhalation. Depending on the nebuliser system, the output quantity from the nebuliser can be affected. The deposition of the medicament aerosol in the lungs is also influenced by the breathing manoeuvre. Reference is made in this regard to the published literature by W. Bennet "Controlled inhalation of aerosolised therapeutics", Expert Opinion Drug Delivery, 2005, 2(4):763-767, Ashley Pub., and Peter Brand "Total Deposition of therapeutic particles during spontaneous and controlled inhalations", Journal of Pharmaceutical Sciences, Vol. 89, No. 6, June 2000.

Different requirements for inhalation can be established depending on the liquid medicament, the nebuliser system and the medicament aerosol resulting therefrom. Furthermore, owing to his breathing manoeuvre and lung morphometry, the patient influences the success of inhalation, and different degrees of side effects can accordingly result.

The aerosol therapy device of the present invention comprises a housing. The housing can be formed in one or more parts. An aerosol generator is furthermore arranged in the housing and serves to nebulise the liquid mentioned above. Also formed in the housing is an air inlet, which is disposed upstream of the aerosol generator, and an air outlet, which is formed downstream of the aerosol generator to administer the generated aerosol. A flow path is formed between the air inlet and the air outlet, along which air introduced via the air inlet can flow past the aerosol generator to the air outlet. As regards the terminology "upstream" and "downstream" as well as "inlet" and "outlet", reference is made to the flow during administration of the generated aerosol, i.e. during an inhalation cycle (breathing in) of a user. During inhalation, a negative pressure is thereby generated at the air outlet, which induces a flow of air from the air inlet to the air outlet, said flow bypassing the aerosol generator in the form of an enveloping flow. The present invention is characterised in particular in that a frustoconical flow channel is disposed between the aerosol generator and the air outlet, the central axis of which extends in a curved manner. The flow channel therefore has a tapering horn shape, with a smaller opening cross-section on the side of the air outlet and a larger opening cross-section on the side of the aerosol generator. The central axis is hereby preferably curved continuously, for example along a circular path. The flow channel preferably completely bridges the section between the aerosol generator and the air outlet. As a result of the structure according to the invention, flow guidance takes place with as little turbulence, swirl or cross-flow as possible. Owing to this flow optimisation, it is achieved that as little aerosol as possible is deposited on the inner walls of the flow channel, by which amount the quantity of aerosol emitted at the air outlet would be reduced. Thus, the design according to the invention allows a relatively constant output rate (Total Output Rate, TOR) to be realised at the air outlet, namely independently of the respective breathing manoeuvre and hence of the user. That is to say, at a predetermined starting volume of the liquid to be nebulised, an output of approximately 70% to 85% of the starting volume can be realised irrespective of the user. Depending on the design of the frustoconical flow channel, the output values are thereby greater than 60% and generally have low variances of less than 15%. That is to say, at a higher flow rate (flow velocity), minimally more aerosol is deposited in the housing between the aerosol generator and the air outlet than in the case of a lower flow rate. Therefore, the associated differences in the flow velocity have a subordinate effect on aerosol deposition in the interior of the device as compared to the variable inhalation/exhalation ratios.

It has proven to be particularly preferred for the central axis to be curved with a radius of curvature in the range of between 40 mm and 60 mm, preferably between 45 mm and 55 mm and most preferred between 48 mm and 52 mm. As a practical possibility, a radius of curvature of 50 mm has proven to be advantageous.

Preferably used as the aerosol generator is a membrane generator having a vibratable membrane with a plurality of openings, whereby the liquid is nebulised through the openings upon vibration of the membrane. The membrane is a flat and even element that lies in a plane which forms an angle of between 65° and 85°, preferably between 70° and 80° and most preferred between 73° and 77°, with a plane in which an air outlet opening (cross-sectional area) of the air outlet lies. 75° has hereby proven to be the preferred realisable angle. This angle is preferably realised solely by the curved frustoconical flow channel, as a result of which the dispersion of the aerosol generated by the aerosol generator can be optimised.

It is hereby particularly preferred for the membrane to extend parallel to the base surface of the frustoconical flow channel and for the flow channel to substantially directly adjoin the membrane. In other words, it is preferred for the flow channel to form the aerosol mixing chamber, into which the aerosol generator nebulises, in the region of its base surface so that the airflow from the air inlet to the air outlet takes the aerosol with it on its path to the air outlet.

For a uniform acceleration and generation of a nozzle flow (equalisation of the airflow) during inhalation irrespective of the suction force, it is furthermore advantageous to set the ratio of the base surface to the upper surface of the frustoconical flow channel or of the base surface of the frustoconical flow channel to the cross-section of the air outlet at between 1.5 and 3.0, preferably between 1.8 and 2.5 and most preferred between 1.95 and 2.15. For example, the flow channel can have a base surface with a diameter of, for instance, approximately 37 mm, and an upper surface with a diameter of, for instance, approximately 18 mm. Alternatively, an elliptical cross-section that tapers from the base surface towards the air outlet can also be selected.

According to a further advantageous embodiment, a valve arrangement is disposed between the air inlet and the aerosol generator, which only allows the flow of air in the direction from the air inlet towards the air outlet (one-way or non-return valve), with an expansion chamber (buffer) being formed between the valve arrangement and the aerosol generator, preferably directly adjoining the aerosol generator. In the expansion chamber, the air which flows in during inhalation is calmed directly prior to the aerosol generator, i.e. turbulence is reduced before the aerosol generator is bypassed in the form of an enveloping flow. This feature therefore further contributes to the prevention of turbulence downstream of the aerosol generator, in particular in the immediate vicinity of the aerosol generator, so as to also minimise in this manner depositions in the housing of the aerosol therapy device.

It has thereby proven to be particularly advantageous for the volume of the expansion chamber to be in a range of between 8 ml and 18 ml, preferably 10 ml and 16 ml and most preferred between 12 ml and 14 ml. This is an elected compromise between a theoretically large expansion chamber that optimally calms the air, i.e. reduces turbulence, and a small structure of the inhalation device that allows for mobile use.

A mouthpiece having an elliptical cross-section can furthermore connect to the frustoconical flow channel. The mouthpiece thereby forms the interface to the user. The mouthpiece can alternatively also be replaced by a respiratory mask. At least one non-return valve is preferably provided in the housing in the region of the tapering from the preferably circular cross-section of the upper surface of the frustoconical flow channel to the elliptical cross-section of the mouthpiece. A flow into the housing via the non-return valve is not possible, however, a flow of air from the air outlet out of the housing is possible via the non-return valve. During exhalation, this non-return valve serves to conduct the exhaled air out of the housing of the aerosol therapy device as directly as possible without transporting out too much newly generated aerosol, and without aerosol production being adversely affected or deposition losses occurring owing to turbulence. By arranging the valve and mouthpiece in a tangential extension of the curved frustoconical flow channel, the formation of flow conditions in the region of the non-return valve that force an emission of the aerosol out of the frustoconical flow channel via the non-return valve is prevented. Owing, inter alia, to this special arrangement, it was possible to reduce the aerosol losses during continuous aerosol generation and during continued inhalation and exhalation to approximately 6% of the starting liquid volume. The tapering, flow-favourable design of the frustoconical flow channel also contributes in this respect.

According to a preferred embodiment, the frustoconical flow channel has a volume of 30 ml to 50 ml, preferably 35 ml to 45 ml and most preferred of 39 ml to 42 ml.

According to a preferred embodiment, the flow rate is detected at a point in the flow channel of the interior of the device, and the control is designed such that it terminates aerosol generation by the aerosol generator upon reaching a desired maximum dose. An aerosol generator having a vibratable membrane has a constant output rate at a predetermined operating power, and the desired dose can be determined by way of time control and flow rate measurement. It could be conceivable here, for example, that a desired dosage to be administered is input into the aerosol therapy device by means of an input device. The control thereupon calculates the necessary inhalation time and/or inhalation volume in order to achieve the input dosage and detects the flow rate continuously and/or at predetermined time intervals. If the calculated inhalation time for the corresponding dosage is reached, aerosol generation is stopped. The corresponding dose has been administered at this point in time. Similar designs are obviously also conceivable when detecting volume or time.

Further advantages and features of the present invention, which can be realised individually or in combination with one or more of the aforementioned features, are apparent from the following description of a preferred embodiment, which occurs with reference to the accompanying drawings:

FIG. 4 shows the measurement results when using the aerosol therapy device shown in FIGS. 1 and 2 with different breathing manoeuvres and different aerosol generators.

Figure 1:
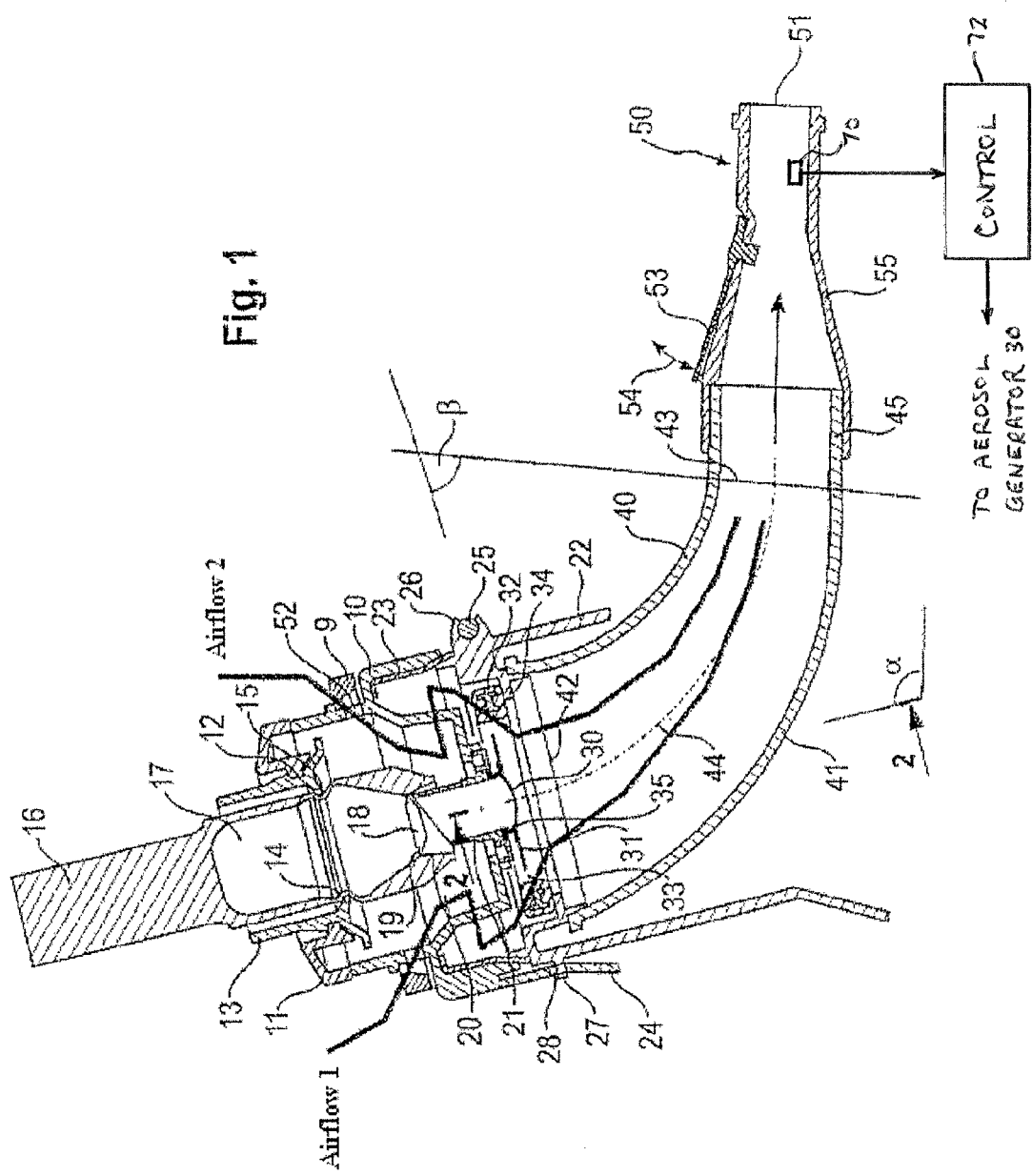
FIG. 1 shows a longitudinal section through an aerosol therapy device according to the invention.

The aerosol therapy device shown in FIG. 1 comprises a multi-part housing. The housing is composed of a base body 10 and a lid 11 that is connected to the base body 10 by means of screw threads and is rotatable relative to the base body 10. The lid 11 comprises pins 12 which project radially inwards and engage in a thread of an ampoule holder that is guided into the lid 11 in a translatory manner. The ampoule holder 13 furthermore comprises projections 14 which face radially inward and engage in a circumferential groove 15 of an ampoule 16 such that the ampoule is detachably retained in the ampoule holder. The ampoule 16 comprises a reservoir 17 that contains the liquid to be nebulised as well as a volume of air. The liquid-to-air ratio can hereby be set so as to achieve a nebulisation by the aerosol generator 30 of the liquid disposed in the reservoir 17 that is as uniform as possible over time until the end of nebulisation. The ampoule 16 furthermore comprises a bottom 18 having a surrounding predetermined break point 19 as well as a collar 20 extending from the bottom 18 and beyond the same.

A hollow piercing spike 21 is furthermore connected to the base body 10 of the housing in order to pierce the surrounding predetermined break point 19 of the ampoule 16 and make the substance contained in the reservoir 17 available to the aerosol generator 30. The surrounding collar thereby seals against the piercing spike and assumes a guiding function when opening the ampoule. The ampoule is not pierced in the drawings shown in FIGS. 1 and 2, i.e. there is still no communication between the aerosol generator 30 and the reservoir.

As a further component, the housing comprises a stand 22, which is designed for standing the aerosol therapy device on a flat, horizontal surface such as a table. The stand 22 is thereby preferably designed such that the membrane 31 of the aerosol generator 30 forms an angle of between 30° and 10° to the horizontal, preferably 17.5° to the horizontal. That is to say, the angle α of a straight line perpendicular to the plane of membrane 31 of the aerosol generator 30 to a horizontal line is approximately 107.5° or alternatively the adjacent angle is approximately 72.5°. The stand 22 can preferably be connected with the base body 10 by means of a seal 23. For this purpose, it is preferred to provide an engaging element 25, for example in the form of a bolt-shaped member, on the base body 10 and to also arrange a clip-on element 26 on the stand 22, which has a corresponding design to the engaging element 25. It is furthermore envisaged to design the engaging element 26 and the engaging element 25 diametrically opposite a snap-in hook 24 and a corresponding counter-piece 27 on the base body 10 and the stand 22, respectively. By clipping the clip-on element 26 onto the engaging element 25 and pivoting the stand 22 about the engaging element 25, it is possible to lock the engaging element 27 (projection) in the snap-in hook 24 of the base body 10, which comprises a recess 28, and thereby achieve a connection between the base body 10 and the stand 22, in which the two components are pressed against one another via the seal.

The aerosol generator 30 is preferably a membrane generator. In the shown embodiment, it comprises a membrane 31 having a plurality of tiny openings or holes in the micro range, which completely penetrate the membrane. The membrane 31 can preferably be vibrated by means of a piezoelectric element, i.e. it can be caused to oscillate. Owing to the oscillation of the membrane, liquid on one side of the membrane, i.e. from reservoir 17, which is made available to one side of the membrane 31 via the hollow piercing spike 21, will pass through the openings (not shown) and be nebulised on the other side of the membrane 31 in a mixing chamber which will be described below. This general principle is explained, for example, in U.S. Pat. No. 5,518,179, and thus a detailed description of this mode of function is not provided here.

According to the invention, the membrane 31, which is a flat and even element possibly with a dome shape in the centre, i.e. it defines a plane, is held in a frame 32 by means of spokes 70. Both the membrane 31 and the frame 32 are designed so as to be substantially circular or annular. According to the present embodiment, the frame 32 is coated with a soft resilient material which is the same as or similar to the material of the seal 23. This coating of the membrane 31 was realised as an embodiment by way of direct insert moulding in a two-component plastic injection moulding process. With the exception of the spokes along the entire circumference of the membrane, a clearance 33 is formed between the membrane 31 and the radially inner circumferential surface of the frame 32 surrounding the membrane 31, which consists of the frame and the coating, said clearance 33 forming a passage for the airflow described below in order to generate the cited enveloping flow. In order to assemble the aerosol generator 30, a shoulder 34 is provided in the stand 22, on which the aerosol generator 30 or the frame 32 with the coating can be placed. A sealing member 35 having at least one surrounding resilient sealing lip is also provided on the base body 10 facing the aerosol generator 30 in the region of the piercing spike 21. Upon assembly, the membrane 31 and at least the region of the membrane 31 comprising the tiny openings becomes completely surrounded by the sealing lip of the sealing member 35 so that liquid from the reservoir 17 can be supplied to the membrane region with the tiny openings via the spike 21 without liquid escaping at the interface between the seal 35 and the membrane 31. During assembly, the membrane 30 is pressed against the sealing member 35 via the shoulder 34 and the locking of the stand 22 to the base body 10 so as to achieve a sufficient seal.

The housing furthermore comprises a flow diverter 40 which can be connected to the stand 22 by means of a type of bayonet catch (not shown). The flow diverter 40 forms a frustoconical flow channel 41. The base surface 42 of the frustoconical flow channel 41 thereby extends substantially parallel to the plane of the membrane 31 and substantially adjoins directly thereto. On the other hand, the upper surface 43 of the frustoconical flow channel 41 extends in the shown embodiment at an angle of 75° to this plane or to the base surface 42, as is shown by the angle β in FIG. 1. The base surface 42 has a circular cross-section with a diameter of approximately 37 mm, whereas the upper surface 43 has a circular cross-section with a diameter of approximately 18 mm (The measurements each relate to the respective internal diameter). The ratio of the base surface 42 to the upper surface 43 is therefore 2.05. The frustoconical flow channel 41 comprises a central axis 44, which extends along a circular path in the shown embodiment and is thus curved continuously. In the shown embodiment, the radius of curvature of the central axis is 50 mm.

Adjoining the upper surface 43, more specifically continuing from this area in a tangential manner, the flow diverter 40 comprises a cylindrical interface 45 with a circular cross-section that corresponds to the cross-section of the upper surface 43. This interface 45 is used for the assembly of a mouthpiece 50 which is also a part of the housing. The mouthpiece can preferably be held on the interface 45 by means of a pure frictional connection so that it can be easily exchanged and, for example, sterilised. In the shown embodiment, the mouthpiece 50 furthermore serves to modify the circular cross-section in the region of the upper surface 43 of the flow diverter 40 to an ergonomically shaped elliptical cross-section at the air outlet 51. In the longitudinal section shown in FIG. 1, a tapering thereby occurs in the direction of the air outlet 51. A non-return valve 53 is disposed in the region of this tapering, which opens and closes in the direction of the arrow 54. During exhalation, this non-return valve 53 helps to enable a flow of air via the air outlet 51, through the valve 53 and out of the housing, and thus an escape of the exhaled air from the housing. Owing to the arrangement of the valve and the mouthpiece as a tangential extension of the tapering, curved flow channel, flow conditions are generated during exhalation which reduce the amount of aerosol carried out of the region between the aerosol generator 30 and the non-return valve 53 via the non-return valve 53. During exhalation, the exhaled air is not breathed back into the aerosol mixing chamber 41, but is rather guided directly out of the housing prior to the flow diverter 40 of the housing without any disturbing influences on the aerosol disposed in the frustoconical flow channel and without thereby also transporting newly generated aerosol out of the housing. This aerosol is instead concentrated in the frustoconical flow channel like in a mixing chamber and is therefore available for the next inhalation as a concentrated aerosol cloud, quasi as an aerosol bolus.

A plurality of openings 52 that act as air inlets are provided in the base body 10 in the region of the screw threads into which the radially protruding projections 9 of the lid 11 engage. These air inlets can also be seen in FIG. 2. A valve arrangement 60 is also apparent in FIG. 2, which can be formed from one or more valve flaps 61. These valve flaps are preferably designed such that they are pivotable about a pivot axis 62 and lie on a valve seat 65 in a sealing manner in the closed valve state. They are arranged so as to allow a flow of air from the air inlet 52, around the aerosol generator 30, and up to the air outlet 51 but not, however, in the opposite direction. A first space 64 is formed between the air inlet 52 and the valve arrangement 60. Upon inhalation, air flows out of the space 64 and into a further space 63 via the valve arrangement 60, which opens in this case. The space 63 hereby forms an expansion chamber that acts as a buffer and in which the airflow first of all calms and slows down. In the embodiment shown as an example, a volume of, for instance, 13 ml is provided for the expansion chamber.

The valve arrangement 60 can furthermore also be provided in such a manner that it limits the flow of air into the expansion chamber 63 depending on the negative pressure at the air outlet 51 during inhalation. For example, when opening, the valve flap 61 may first of all abut a first stop (not shown), as a result of which a first flow cross-section is formed between the valve flap 61 and the valve seat 65. If the suction force is increased, it is conceivable for the then flexible valve flap 61 to slide over the first stop and encounter a second stop, against which the side of the valve flap 61 which is opposite the valve seat 65 forms a seal. In this case, a second flow cross-section is formed between the stop and, for example, an outer surface of the base body 10, with this second flow cross-section being smaller than the first one such that the flow rate is reduced and a larger flow resistance is formed.

As a further embodiment, the valve arrangement 60 may also be provided as a separate component that acts as a valve which limits the respiratory flow. This valve is arranged at the inlet openings in such a manner that a negative pressure in the nebulisation space moves the valve member in order to expose the inlet openings. The movement of the valve member is limited such that the exposure of the inlet openings is substantially proportional to the negative pressure only up to a threshold value of the negative pressure in the nebulisation space. For a more accurate description, reference is made to DE 101 26 807 and EP 0 895 788.

A flow sensor 70 may be arranged in a region of the air outlet 51. The flow sensor 70 detects the airflow at the air outlet 51. A control 72 is designed to control the aerosol generator 30 based on the detected airflow. The flow sensor 70 may detect the flow rate at the air outlet 51, and the control 72 may be designed such that it terminates aerosol generation by the aerosol generator 30 upon reaching a maximum flow rate.

The mode of function of the shown and described aerosol therapy device will be explained in the following with reference to FIGS. 1 and 2.

During use, a patient places the mouthpiece 50 in his mouth and commences a breathing manoeuvre. Upon inhalation, a negative pressure is generated at the air outlet 51, as a result of which the valve flap 61 opens. External air thereby flows into the space 64 via inlets 52, through the valve flaps 61 into the expansion chamber 63, past the aerosol generator 30 and up to air outlet 51 via the frustoconical flow channel 41 which extends in a curved manner. During this time, the aerosol generator 30 continuously generates an aerosol that mixes with the air in the region of the base surface 42 and is dispensed via the flow channel 41. When the user starts to exhale, a flow in the opposite direction is induced. Owing to the positive pressure (dynamic pressure) which thereby results, the inlet valves 61 close and prevent the aerosol cloud from retreating upstream of the aerosol generator into the expansion chamber 63. During this time, a new aerosol bolus (concentrated aerosol) can form between the base surface 42 and the air outlet 51 in the region of the flow diverter 40. At the same time, the non-return valve 53 opens so as to ensure that the exhaled air flows out of the housing along the most direct path without too large an amount of aerosol exiting the housing of the aerosol therapy device via the non-return valve 53. Turbulent mixing and thus a flushing of the aerosol cloud out of the frustoconical flow channel are virtually prevented. A new inhalation cycle subsequently follows, in which the aerosol bolus in the curved flow channel 41 is first of all discharged in its entirety and only then is the air flowing in via air inlets 52 and valve arrangement 60, which is continuously mixed with aerosol, inhaled. This process is repeated until the end of the therapy session.

Figure 2:
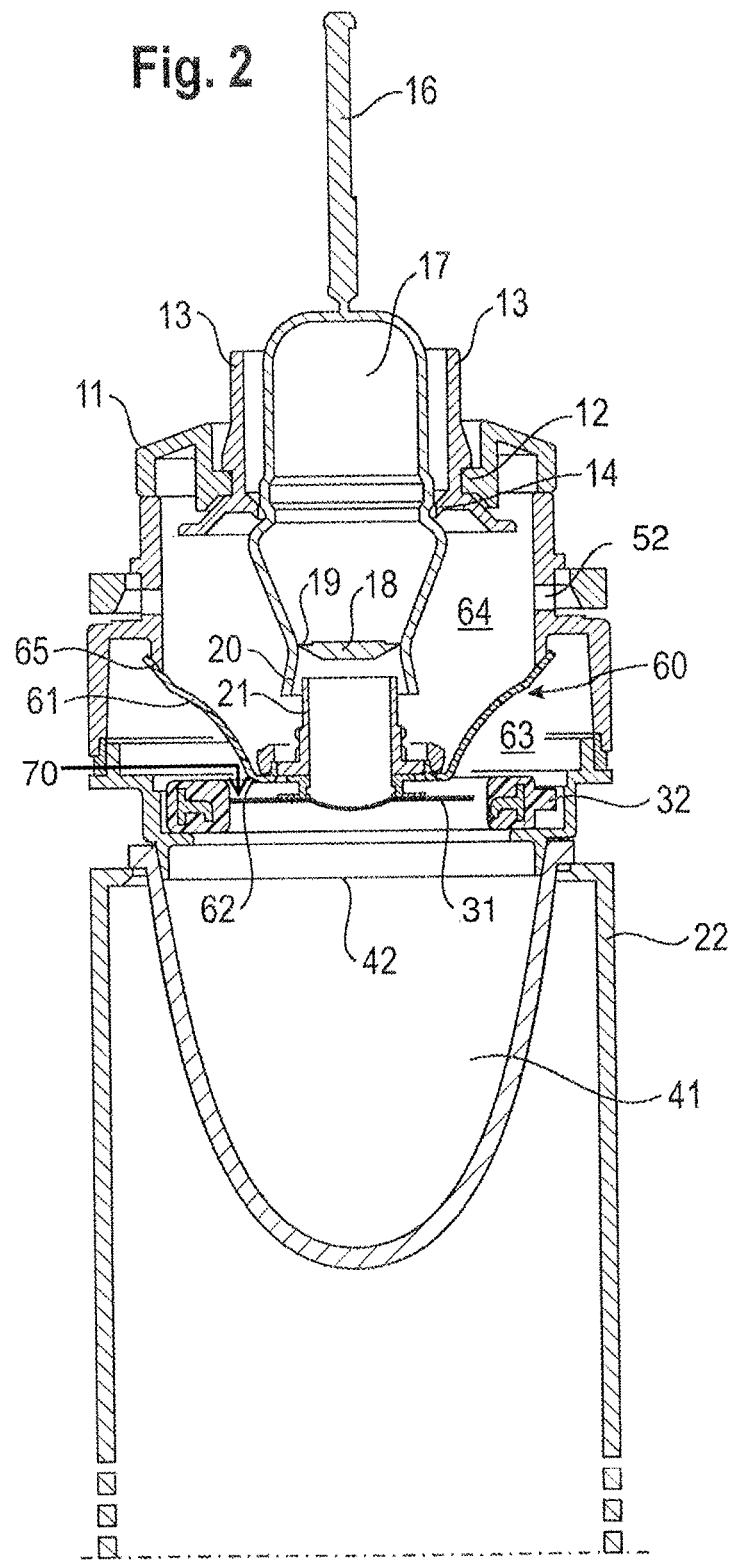
FIG. 2 shows a section through the aerosol therapy device shown in FIG. 1 along line 2-2.

In tests using an aerosol therapy device such as shown in FIGS. 1 and 2, different breathing manoeuvres were simulated by means of a respiratory pump. A breathing manoeuvre was thereby simulated for an average adult having a maximum flow of 24 l/min (volume 500 ml, inhalation ratio In:Ex=50:50, 15 breaths/min), for an adult with emphysema having a maximum flow of 42 l/min (volume 450 ml, inhalation ratio In:Ex=30:70, 17 breaths/min) and for an average healthy child approximately 6 years old having a maximum flow of 12 l/min (volume 150 ml, inhalation ratio In:Ex=40:60, 20 breaths/min) (cf. FIG. 3).

Figure 3:
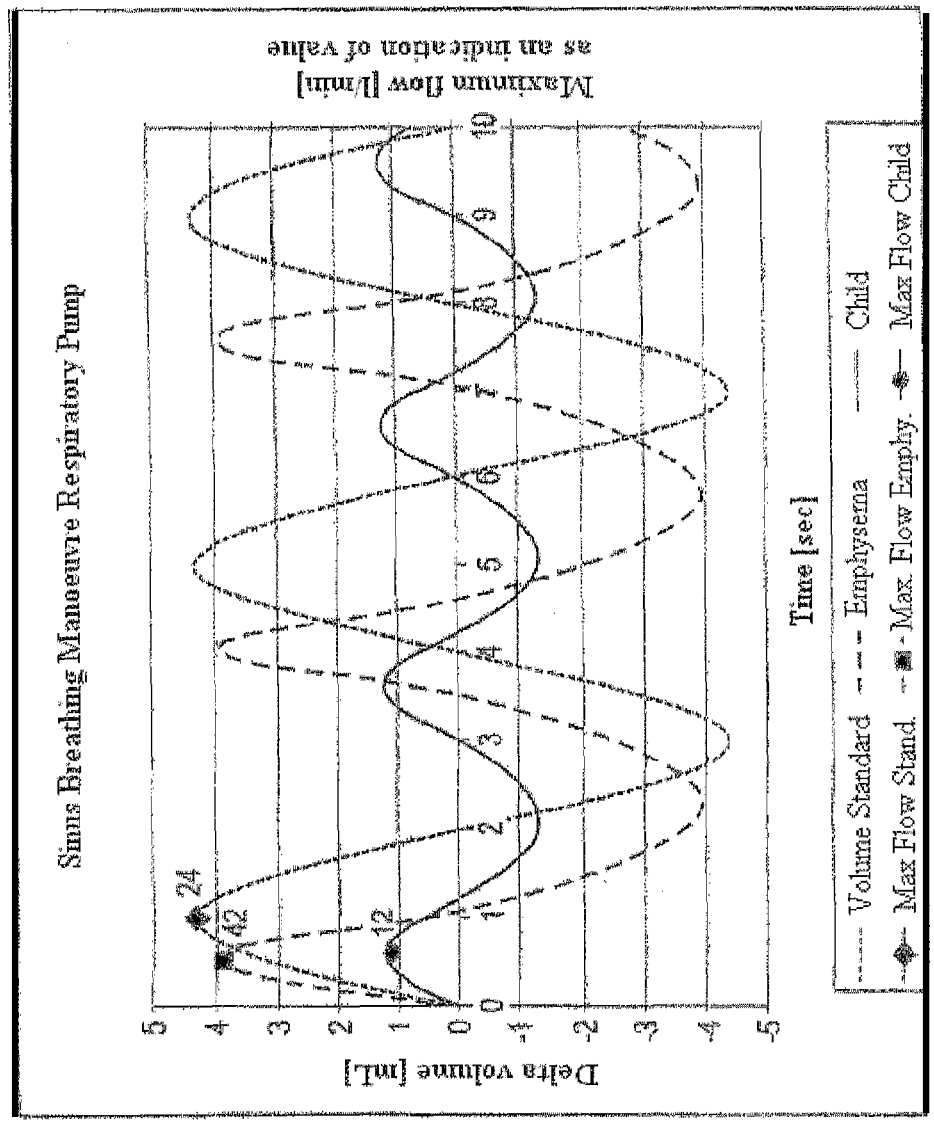
FIG. 3 shows, by way of an example, the differences in the breathing manoeuvres of three different simulated users.

An ampoule having a constant filling volume (output amount) was used for the different patient models. At the air outlet 51, the amount of aerosol discharged was collected and determined in relation to the original liquid content of the reservoir 17 of the ampoule until the ampoule was completely empty. This process was repeated for the three different breathing manoeuvres (FIG. 3). The component (exhaled fraction) discharged via the non-return valve 53 was also determined, as was the component (Depo Mk) deposited in the flow channel 41 and the residual component (Depo Res) in the medicament reservoir or in the ampoule. The test was additionally carried out with different aerosol generators which are referred to in FIG. 4 as "30 Head" and "35 Head" and which each have a different median droplet diameter (MMD) of 3.22 µm in the case of the "30 Head" and 3.66 µm in the case of the "35 Head". The average nebulising efficiency in the "30 Head" was 5.7 mg/J and in the "35 Head" was 7.4 mg/J. It was thereby proven that even in the case of different breathing manoeuvres, a relatively constant output at the air outlet 51 can be achieved within a relatively narrow range of variation. During breathing simulation using the 30 Head, aerosol amounts (delivered dose) of between 71.3 and 74% of the starting amount were measured. The deposition in the flow channel 41 as well as the exhaled fraction (via the non-return valve 53) were also relatively low. It also turned out that owing to the inventive arrangement of in particular the flow channel 41, a relatively constant delivered dose can be achieved even when using different aerosol generators with different aerosol generation rates. In other words, an aerosol therapy device according to the present invention enables a largely constant medicament dosage to be administered in aerosol form in a very simple manner and without complicated electronic controls, and this can take place both irrespective of the respiratory pattern of the user and of the specification of the aerosol generator used. Such a high dosage accuracy is extremely important for some medicaments and was previously only possible in complex, respiration-controlled nebulisers, not however during continuous nebulisation.

However, it goes without saying that the present invention is not limited to this explicit embodiment and is in particular not restricted to the described dimensions. Deviations in the radius of curvature, the incline of the membrane of the aerosol generator, the ratio between the base surface and the upper surface of the flow channel as well as in the volumes of the expansion chamber and flow channel, as explained above, are rather also conceivable.

The present aerosol therapy device can furthermore be used for the administration of the active substance classes and substances listed below:

The active compounds include, for example, substances which are selected from the group consisting of anti-inflammatory compounds, glucocorticoids, beta-agonists, anticholinergic agents, phosphodiesterase inhibitors, anti-allergic medicaments, antihistamines, antioxidants, vitamins, retinol, leukotriene antagonists, anti-infective agents, antibiotics, antifungal agents, antiviral agents, mucolytic agents, decongestants, antiseptics, mast cell stabilisers, cytostatic agents, immunomodulators, vaccines, wound-healing agents, local anaesthetics, platelet-activating factor inhibitors, potassium channel openers, testosterone derivatives, tachykinin and kinin antagonists, interferons, vasodilators, vasoconstrictors, angiotensin converting enzyme (ACE) inhibitors, antidepressants, agents for influencing signal transmission between cells, heparinoids, α antitrypsin, lung surfactants, prostaglandins, endothelin receptor antagonists, vasoactive intestinal peptides, serotonin receptor antagonists, statins, calcium antagonists, oligonucleotides, peptides, proteins, phosphorimidon, plant extracts and substances obtained from fungi.

Examples of possibly useful anti-inflammatory compounds are glucocorticoids such as alclomethasone, amcinonide, betamethasone, beclomethasone, budesonide, ciclesonide, clobetasol, clobetasone, clocortolone, desonide, dexamethasone, desoxymethasone, diflorasone, diflucortolone, fluoconolone acetonide, flucinonide, fludroxycortide, flumetasone, flunisolide, fluticasone, fluocinonide, fluocortin butyl, fluocortolon, fluprednidene, halcinonide, halometasone, hydrocortisone, hydroxycortisone, icomethasone, methylprednisolone, mometasone, prednicarbate, prednisolone, prednisone, rofleponide and triamcinolone acetonide; non-steroidal glucocorticoid receptor activators such as, for example, dehydroepiandrosterone and derivatives such as dehydroepiandrosterone sulphate (DHEAS); non-steroidal anti-inflammatory medicaments (NSAIDs) such as, for example, aceclofenac, acemetacin, bromfenac, diclofenac, etodolac, ibuprofen, indometacin, nabumetone, sulindac, tolmetin, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, lornoxicam, meloxicam, piroxicam, tenoxicam, celecoxib, etoricoxib, lumiracoxib, parecoxib, rofecoxib, valdecoxib, lodine, nimesulide and licofelone; prostaglandin receptor inhibitors; 5-lipoxygenase inhibitors such as zileuton; 5-lipoxygenase activating protein inhibitors; leukotriene receptor antagonists such as, for example, pobilukast, montelukast, pranlukast, roflumilast and zafirlukast; bradykinin receptor antagonists; matrix metalloproteinase (MMP) inhibitors; anti-inflammatory monoclonal antibodies; and TNF receptor inhibitors; including any pharmaceutically acceptable salts, esters, isomers, stereoisomers, diastereomers, epimers, solvates or other hydrates thereof, prodrugs, derivatives or any other chemical or physical forms of active compounds comprising the respective active residues.

The class or therapeutic category of anti-infective agents is comprehensively understood herein as comprising compounds which are effective against bacterial, viral, fungal and protozoal infections, i.e. compounds encompassing the classes of antimicrobial agents, antibiotics, anti-viral agents, anti-fungal agents, anti-protozoal agents and antiseptics.

Examples of possibly useful antibiotics are penicillins, combined or not combined with beta-lactamase inhibitors (such as clavulanic acid, sulbactam and tazobactam), including narrow-spectrum penicillins such as benzylpenicillin, phenoxymethylpenicillin, benzathine benzylpenicillin, procaine benzylpenicillin, clemizole benzylpenicillin, dibenzyletylenediamine benzylpenicillin; narrow-spectrum penicillinase-resistant penicillins such as methicillin, oxacillin, cloxacillin, dicloxacillin, flucloxacillin, nafcillin, propicillin, mecillinam; narrow-spectrum beta-lactamase-resistant penicillins such as temocillin; and extended-spectrum penicillins such as ampicillin, amoxicillin, bacampicillin, pivampicillin, ticarcillin, azlocillin, piperacillin, apalcillin, carbenicillin, mezlocillin and pivmecillinam;

cephalosporins, including first generation cephalosporins such as cefacetrile, cefadroxil, cefalexin, cephaloglycin, cefalonium, cefaloridine, cefalotin, cefapirin, cefatrizine, cefazaflur, cefazedone, cefazolin, cefradine, cefroxadine, ceftezole; second generation cephalosporins such as cefonicid, cefprozil, cefuroxime, cefuroxime-axetil, cefuzonam, cefaclor, cefamandole, ceforanide, cefotiam, cefotiam-hexetil, loracarbef, cefbuperazone, cefmetazole, cefminox, cefotetan, cefoxitin; third generation cephalosporins such as cefcapene, cefdaloxime, cefdinir, cefditoren, cefetamet, cefetametpivoxil, cefixime, cefmenoxime, cefodizime, cefoperazone, cefotaxime, cefpimizole, cefpodoxime, cefpodoxime-proxetil, cefteram, ceftibuten, ceftiofur, ceftiolene, ceftizoxime, ceftriaxone, ceftazidime, cefpiramide, cefsulodin, latamoxef; fourth generation cephalosporins such as cefclidine, cefepime, cefluprenam, cefoselis, cefozopran, cefpirome, cefquinome, flomoxef; and further cephalosporins such as cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, ceftioxide, cefuracetime and ceftobiprole;

carbapenems, including imipenem, imipenemcilastatin, meropenem, doripenem, faropenem, tebipenem, ertapenem, panipenem, biapenem and ritipenem;

monobactams, including aztreonam;

aminoglycosides such as amikacin, apramycin, arbekacin, capreomycin, gentamicin, hygromycin B, isepamicin, kanamycin, mupirocin, neomycin, netilmicin, paromomycin, spectinomycin, streptomycin and tobramycin;

macrolides, including erythromycin, azithromycin, clarithromycin, dirithromycin, dithromycin, roxithromycin, troleandomycin, carbomycin A, josamycin, kitasamycin, oleandomycin, spiramycin, tylosin, midecamycin, rapamycin, miocamycin, fluritromycin, rokitamycin, rosaramycin and telithromycin;

gyrase inhibitors or fluoroquinolones, including first generation fluoroquinolones such as nalidixic acid, oxolinic acid and piromidic acid; second generation fluoroquinolones such as cinoxacin, flumequine, novobiocin, pipemidic acid and rosoxacin; third generation fluoroquinolones such as enoxacin, norfloxacin, nadifloxacin, ciprofloxacin, ofloxacin, fleroxacin, lomefloxacin, pefloxacin, temafloxacin and uvofloxacin; and fourth generation fluoroquinolones such as balofloxacin, caderofloxacin, clinafloxacin, difloxacin, garenoxacin, gatifloxacin, gemifloxacin, grepafloxacin, levofloxacin, moxifloxacin, olamufloxacin, pazufloxacin, rufloxacin, sitafloxacin, sparfloxacin, tosufloxacin, trovafloxacin, ecinofloxacin and prulifloxacin;

tetracyclines, including tetracycline, chlortetracycline, oxytetracycline, demeclocycline, doxycycline, clomocycline, lymecycline, meclocycline, methacycline, minocycline, penimepicycline, rolitetracycline, chelocardin, sancycline, apicycline, guamecycline, meglucycline, mepylcycline, pipacycline, etamocycline, penimocycline and tigecycline;

glycopeptides, including vancomycin, teicoplanin, ristocetin, avoparcin, oritavancin, ramoplanin, decaplanin and peptide 4;

polymycins, including polymyxin B, colistin and surfactin;

lincosamides, including lincomycin and clindamycin;

streptogramins, including dalfopristin, quinupristin, pristinamycin and virginiamycin;

phenicols, including chloramphenicol, tiamphenicol and florphenicol;

rifamycins, including rifampicin, rifabutin, rifapentine and rifaximin;

nicotinic acid derivatives, including isoniazid, ethionamide, prothionamide and pyrazinamide;

nitroimidazoles, including metronidazole, timidazole, nimorazole and ornidazole;

nitrofurans, including nifurfolin, nifuroxazide, nifuroxima, nifurzide, nitrofurantoin and nitrofurazone;

sulfonamides, including sulfacarbamide, sulfamazole, sulfamazone, sulfamethizole, sulfametopirazine, sulfametoxypiridazine, sulfametrole, succinylsulfathiazole, sulfisoxazole, sulfamethoxazole, sulfadiazine, phtalylsulfacetamide, phthalylsulfonazole, phtalylsulfathiazole, sulfasalazine, sulfoguanidine, sulfacetamide, silver sulfadiazine, mafenide acetate, sulfadoxine, sulfalene, cotrimoxazole, cotrimetrol, cotrimaxine and cotetroxacin;

other antibiotics, including plectasin, dalbavancin, daptomycin, ramoplanin, telavancin, bacitracin, tyrothricin, tygecycline, oxazolidinones (such as linezolid), fosfomycin, cycloserine, terizidone, inhibitors of dihydropteroate synthetase, sulfones, p-aminosalicylic acid, 2,4-diaminopyrimidines (such as bromodiprim, pyrimethamine, tetroxyprim), trimethoprim, ranbezolid, ethambutol, dapsone, fucidinic acid, terizidone, ansamycin, lysostaphin, iclaprim, mirocin B17, clerocidin, filgrastim and pentamidine;

Examples of potentially useful antifungal agents are allylamines and thiocarbamates, including terbinafine, amorolfine, naftifine, butenafine, tolciclate and tolnaftate; polyenes, including amphotericin B, natamycin, nystatin, flucocytosine and rimocidin; azoles and triazoles, including bifonazole, clotrimazole, croconazole, econazole, fenticonazole, isoconazole, miconazole, oxiconazole, sertaconazole, tioconazole, butoconazole, sulconazole, tioconazole, fluconazole, itraconazole, ketoconazole, voriconazole, ravuconazole, posaconazole, isavuconazole and terconazole; echinocandins, including micafungin, caspofungin and anidulafungin; further antifungal agents, including flucytosine, griseofluvin, ciclopirox olamine, haloprogin and undecylenic acid; including any pharmaceutically acceptable salts, esters, isomers, stereoisomers, diastereomers, epimers, solvates or other hydrates thereof, prodrugs, derivatives or any other chemical or physical forms of active compounds comprising the respective active residues.

Examples of possibly useful antiviral agents are amantadine and derivatives, including tromantadine and rimantadine; neuraminidase inhibitors, including oseltamivir, zanamivir and peramivir; nucleosides, including acyclovir, valaciclovir, penciclovir, famciclovir, brivudine, idoxuridine, trifluridine, vidarabine, ganciclovir, cidofovir, entecavir and valganciclovir; antiretroviral agents, including zidovudine, abacavir, adefovir, didanosine, lamivudine, stavudine, zalcitabine, delavirdine, emtricitabine, efavirenz, loviride, nevirapine, indinavir, nelfinavir, ritonavir, saquinavir, amprenavir, lopinavir, atazanavir, fosamprenavir, tipranavir, darunavir, adefovir, enfuvirtide, loviride and tenofovir; further antiviral agents, including foscarnet, ribavirin, arbidol, docosanol, edoxudine, fomivirsen, fosfonet, ibacitabine, imunovir, imiquimod, inosine, interferons, lysozyme, maraviroc, moroxydine, nexavir, pleconaril, podophyllotoxin, vicriviroc and viramidine; and fixed combinations of antiviral agents, including atripla, combivir, emtricitabine, trizivir and truvada.

Examples of agents that are effective against infections caused by protozans are pentamindine, cotrimoxazole, metronidazole, tinidazole, nimorazole and ornidazole.

Examples of possibly useful antiseptics are acridine derivatives, iodine povidone, benzoates, rivanol, chlorhexidine, quaternary ammonium compounds, cetrimides, biphenylol, chlorophene and octenidine.

Examples of useful prostaglandins are prostacyclin, epoprostenol, treprostinil and iloprost.

Examples of useful endothelin receptor agonists are bosentran, sitaxsentan, ambrisentan and darusentan.

Examples of potentially useful phosphodiesterase (PDE) inhibitors are non-selective methylxantines such as theophylline and pentoxyphylline; and the selective PDE isoenzyme inhibitors such as amrinone, cilostazol, benzafentrine, milrinone, enoximone, motapizone, zardaverine, tolafentrine, rolipram, cilomast, roflumilast, sildenafil, vardenafil and tadalafil.

Examples of beta agonists are short-acting $\beta_2$ sympathicomimetics such as salbutamol (albuterol), levalbuterol, terbutaline, pirbuterol, procaterol, metaproterenol, fenoterol, bitolterol and clenbuterol; and long-acting $\beta_2$ sympathicomimetics such as salmeterol, formoterol, bambuterol, carmoterol, arformoterol, indacaterol and picumeterol.

Examples of potentially useful vasoconstrictors and decongestants which may be useful for reducing swelling of the mucus membrane are alfa-1-sympathicomimetics such as indanazoline, naphazoline, oxymetazoline, tetryzoline, tramazoline, xylometazoline, phenylephrine, fenoxazoline, epinephrine, ephedrine, isoprenaline and hexoprenaline.

Examples of anticholinergic agents are short-acting anticholinergic agents such as ipratropium, oxitropium and trospium; and long-acting anticholinergic agents such as tiotropium, revatropate, glycopyrronium and aclidinium.

Examples of useful immunomodulators are the above named glucocorticoids and non-steroidal glucocorticoid receptor activators; immunosuppressive monoclonal antibodies such as omalizumab, infliximab, adalimumab and etanercept; cyclosporine, tacrolimus, sirolimus (rapamycin), mycophenolate, dimethyl fumarate, ethyl hydrogen fumarate, methotrexate, azathioprine, interferons (alpha, beta, gamma), tumour necrosis factors, cytokines, interleukins, echinacea extract and pelargonium extract.

Examples of possibly useful mucolytic agents are acetylcysteine, ambroxol, bromhexine, carbocysteine, gluthatione, nacystelyn, dornase alpha, mugwort, bromelain, papain, clerodendrum, guaifenesin, cineol, guaiacol, myrthol, mesna, P2Y2-agonists (such as denufosol), heparinoids, sodium chloride, medicaments that influence the uptake of chloride and sodium, such as, for example, N-(3,5-diamino-6-chloropyrazine-2-carbony)-N'-{4-[4-(2,3-dihydroxy-propoxy)-phenyl]butyl}-guanidine-methanesulfonate (PARION 552-02), tyloxapol, lecithin and recombinant lung surfactant proteins.

Examples of useful antihistamines are diphenhydramine, carbinoxamine, doxylamine, clemastine, dimenhydrinate, pheniramine, chlorphenamine, dexchlorphenamine, brompheniramine, triprolidine, cyclizine, chlorcyclizine, hydroxyzine, meclizine, promethazine, alimemazine, cyproheptadine, azatadine, ketotifen, azelastine, levocabastine, olopatadine, epinastine, emedastine, acrivastine, astemizole, cetirizine, loratadine, mizolastine, terfenadine, fexofenadine, levocetirizine and desloratadine.

Examples of mast cell stabilisers are cromoglycate, nedocromil and lodoxamide.

Examples of useful cytostatic agents and metastasis inhibitors are alkylating agents such as nimustine, melphalan, carmustine, lomustine, cyclophosphamide, ifosfamide, trofosfamide, chlorambucil, busulfan, treosulfan, prednimustine, thiotepa, dacarbazine, and complexes of elements of the transition groups (for example, Ti, Zr, V, Nb, Ta, Mo, W, Pt) such as carboplatin, oxyplatin, cis-platin and metallocene compounds such as, for example, titanocene dichloride; anti-metabolites, for example cytarabine, fluorouracil, methotrexate, mercaptopurine, thioguanine, hydroxycarbamide, pemetrexed and gemcitabine; alkaloids such as vinblastine, vincristine, vindesine and vinorelbine; anti-tumour antibiotics such as, for example, aclarubicin, bleomycin, dactinomycin, daunorubicin, doxorubicin, epirubicin, idarubicin, mitoxantrone, mitomycin and plicamycin; and other cytostatic agents such as erlotinib, gefitinib, methotrexate, paclitaxel, docetaxel, amsacrine, estramustine, etoposide, beraprost, procarbazine, temiposide, vandetanib, poly-ADP-ribose-polymerase (PRAP) enzyme inhibitors, banoxantrone, premetrexed, bevacizumab and ranibizumab.

Examples of wound-healing compounds are dexpantenol, allantoin, vitamins, hyaluronic acid, alpha-antitrypsin, inorganic and organic zinc salts/compounds and bismuthselenium salts.

Examples of potentially useful local anaesthetics include benzocaine, tetracaine, procaine, lidocaine and bupivacaine.

Examples of potentially useful antioxidants are superoxide dismutase, acetylcysteine, vitamin C, vitamin E (tocopherols), catalases, reduced glutathione, peroxidases, uric acid, $\beta$-carotene, NOX inhibitors, xanthine oxidase inhibitors, pyruvate and gluconate salts.

Examples of useful plant extracts or ingredients are extracts from chamomile, hamamelis, echinacea, calendula, thyme, papain, pelargonium and pine trees; and essential oils such as myrtol, pinene, limonene, cineole, thymol, menthol, camphor, tannin, alpha-hederin, bisabolol, lycopodine, resveratrol, vitapherole and anti-oxidative ingredients of green tea.

Examples of possibly useful anti-allergic agents include the aforementioned glucocorticoids, mast cell stabilisers, antihistamines, leukotriene receptor antagonists, zileuton, omalizumab and heparinoids.

Examples of useful angiotensin converting enzyme (ACE) inhibitors are captopril, lisinopril, perindopril, trandolapril and cilazapril.

Useful potassium channel openers are, for example, cromakalim, levocromakalim and pinacidil.

Examples of potentially useful tachykinin and kinin antagonists are nolpitantium, saredutant, nepadutant and osanetant.

Antisense oligonucleotides are short synthetic strands of DNA (or analogues) which are complimentary or opposite to the target sequence (DNA, RNA) and which are designed to halt a biological process, such as transcription, translation or splicing. The resulting inhibition of gene expression makes oligonucleotides useful for the treatment of many illnesses, depending on their composition, and numerous compounds are currently being clinically tested, such as, for example, ALN-RSV01 for the treatment of respiratory syncytial virus, AVE-7279 for the treatment of asthma and allergies, TPI-ASM8 for the treatment of allergic asthma and 1018-ISS for the treatment of cancer.

Examples of potentially useful peptides and proteins include amino acids, such as, for example, L-arginine and L-lysine, antibodies to toxins produced by microorganisms, antimicrobial peptides such as cecropins, defensins, thionins and cathelicidins.

For each of these and other explicitly mentioned examples of medicinal substances that are potentially useful for carrying out the invention, the compound names specified herein should be understood as also including any pharmaceutically acceptable salts, esters, isomers, stereoisomers, diastereomers, epimers, solvates or other hydrates, prodrugs, derivatives or any other chemical or physical forms of the respective compounds comprising the respective active residues.

The invention claimed is:

1. An aerosol therapy device comprising:
a housing;
an aerosol generator comprising a vibratable membrane having a plurality of openings through which a substance can be nebulized, the aerosol generator being arranged in the housing;
an air inlet formed in the housing upstream of the aerosol generator; and
an air outlet formed in the housing downstream of the aerosol generator to administer the generated aerosol, with a flow of air from the air inlet to the air outlet, which bypasses the aerosol generator, being generable owing to a negative pressure at the air outlet, wherein a tapered flow channel is disposed between the aerosol generator and the air outlet, wherein the tapered flow channel has a first cross-sectional area at the aerosol generator and a second cross-sectional area, smaller than the first cross-sectional area, at the air outlet, wherein the cross-sectional area of the tapered flow channel continuously decreases from the first cross-sectional area to the second cross-sectional area, wherein the tapered flow channel has a curved central axis, and wherein the tapered flow channel forms a mixing chamber for the aerosol generator in a region of the first-cross sectional area of the tapered flow channel into which mixing chamber the aerosol generator emits the aerosol so that the air flow from the air inlet to the air outlet entrains the aerosol in the air flow to the air outlet and wherein the membrane is held in a frame by spokes defining a clearance between the spokes and between the membrane and an inner circumferential surface of the frame, forming a passage for the air flow bypassing the aerosol generator, wherein the clearance between the membrane and the frame is directly at an outer circumferential edge of the membrane, and wherein the clearance is formed, with the exception of the spokes, along the entire circumference of the membrane between the membrane and the radially inner circumferential surface of the frame.

2. An aerosol therapy device according to claim 1, wherein the central axis is curved with a radius of curvature in the range of between 40 and 60 mm.

3. An aerosol therapy device according to claim 1, wherein the aerosol generator comprises a vibratable membrane having a plurality of openings through which a substance can be nebulised, and the membrane lies in a plane that forms an angle of between 65° and 85°, with a plane in which an air outlet opening (cross-sectional area) of the air outlet lies.

4. An aerosol therapy device according to claim 1, wherein the aerosol generator comprises a vibratable membrane having a plurality of openings through which a substance can be nebulised, and the membrane lies in a plane that extends parallel to the first cross-sectional area of the tapered flow channel.

5. An aerosol therapy device according to claim 4, wherein the tapered flow channel substantially directly adjoins the membrane.

6. An aerosol therapy device according to claim 1, wherein a ratio of a diameter of the first cross-sectional area to a diameter of an upper surface of the tapered flow channel or of the diameter of the first cross-sectional area of the tapered flow channel to a diameter of a the second cross-sectional area of the air outlet is between 1.5 and 3.0.

7. An aerosol therapy device according to claim 1, wherein a valve arrangement is disposed between the air inlet and the aerosol generator, which only allows a flow of air from the air inlet towards the air outlet, and wherein an expansion chamber is formed between the valve arrangement and the aerosol generator.

8. An aerosol therapy device according to claim 1, wherein the volume of an expansion chamber lies in a range of between 8 and 18 ml.

9. An aerosol therapy device according to claim 1, wherein a mouthpiece having an elliptical cross-section attaches to the tapered flow channel, and at least one non-return valve is arranged in a region of a tapering from a circular cross-section of an upper surface of the tapered flow channel to the elliptical cross-section of the mouthpiece, said non-return valve only allowing a flow of air out of the housing from the air outlet via the non-return valve.

10. An aerosol therapy device according to claim 1, wherein the tapered flow channel has a volume of 30 to 50 ml.

11. An aerosol therapy device according to claim 1, wherein a flow sensor is arranged in a region of the air outlet, which detects the airflow at the air outlet, further comprising a control that is designed to control the aerosol generator based on the detected airflow.

12. An aerosol therapy device according to claim 11, wherein the sensor detects the flow rate at the air outlet and the control is designed such that it terminates aerosol generation by the aerosol generator upon reaching a maximum flow rate.

13. An aerosol therapy device according to claim 1, wherein irrespective of a breathing manoeuvre, an emitted aerosol or active substance amount lies in the range of 60% to 99% of the filling amount during continuous aerosol generation.

14. An aerosol therapy device according to claim 1, wherein the central axis is curved with a radius of curvature in the range of between 45 and 55 mm.

15. An aerosol therapy device according to claim 1, wherein the central axis is curved with a radius of curvature in the range of between 48 and 52 mm.

16. An aerosol therapy device according to claim 3, wherein the membrane lies in a plane that forms an angle of between 70° and 80° with a plane in which an air outlet opening (cross-sectional area) of the air outlet lies.

17. An aerosol therapy device according to claim 3, wherein the membrane lies in a plane that forms an angle of between 73° and 77° with a plane in which an air outlet opening (cross-sectional area) of the air outlet lies.

18. An aerosol therapy device according to claim 1, wherein a ratio of a diameter of the first cross-sectional area to a diameter of an upper surface of the tapered flow channel or of the diameter of the first cross-sectional area of the tapered flow channel to a diameter of the second cross-sectional area of the air outlet is between 1.80 and 2.50.

19. An aerosol therapy device according to claim 1, wherein a ratio of a diameter of the first cross-sectional area to a diameter of an upper surface of the tapered flow channel or of the diameter of the first cross-sectional area of the tapered flow channel to a diameter of the second cross-sectional area of the air outlet is between 1.95 and 2.15.

20. An aerosol therapy device according to claim 1, wherein the volume of an expansion chamber lies in a range of between 10 and 16 ml.

21. An aerosol therapy device according to claim 1, wherein the volume of an expansion chamber lies in a range of between 12 and 14 ml.

22. An aerosol therapy device according to claim 1, wherein the tapered flow channel has a volume of 35 to 45 ml.

23. An aerosol therapy device according to claim 1, wherein the tapered flow channel has a volume of 38 to 42 ml.

24. An aerosol therapy device according to claim 1, wherein irrespective of a breathing maneuver, an emitted aerosol or active substance amount lies in the range of 70% to 85% of the filling amount.

25. An aerosol therapy device according to claim 1, wherein the generated aerosol comprises an anticholinergic agent, glucocorticoids, beta agonists, long-acting beta 2 sympathicomimetics, antibiotics, mucolytic agents, immunomodulators, mast cell stabilisers, and/or proteins.

26. An aerosol therapy device according to claim 1, wherein the generated aerosol comprises glycopyrronium, budesonide, formoterol, arformoterol, amikacin, arbekacin, tobramycin, glutathione, dornase alpha, P2Y2-agonists, interferon (alpha, beta, gamma), interleukin, cromoglycate and/or lung surfactant proteins.

27. An aerosol therapy device according to claim 1, further comprising an ampoule, wherein the ampoule comprises an anticholinergic agent, glucocorticoids, beta agonists, long-acting beta 2 sympathicomimetics, antibiotics, mucolytic agents, immunomodulators, mast cell stabilisers, and/or proteins.

28. An aerosol therapy device according to claim 1, further comprising an ampoule, wherein the ampoule comprises glycopyrronium, budesonide, formoterol, arformoterol, amikacin, arbekacin, tobramycin, glutathione, dornase alpha, P2Y2-agonists, interferon (alpha, beta, gamma), interleukin, cromoglycate and/or lung surfactant proteins.

29. An aerosol therapy device according to claim 13, wherein the emitted aerosol comprises glycopyrronium, budesonide, formoterol, arformoterol, amikacin, arbekacin, tobramycin, glutathione, dornase alpha, P2Y2-agonists, interferon (alpha, beta, gamma), interleukin, cromoglycate and/or lung surfactant proteins.

30. An aerosol therapy device according to claim 24, wherein the emitted aerosol comprises glycopyrronium, budesonide, formoterol, arformoterol, amikacin, arbekacin, tobramycin, glutathione, dornase alpha, P2Y2-agonists, interferon (alpha, beta, gamma), interleukin, cromoglycate and/or lung surfactant proteins.

31. An aerosol therapy device according to claim 1, wherein the continuously tapered flow channel is free of air flow obstructions between the aerosol generator and the air outlet.

32. An aerosol therapy device according to claim 1, wherein the housing has a shoulder on which the aerosol generator is placed and a sealing member having at least one surrounding resilient sealing lip facing the aerosol generator, wherein the aerosol generator is pressed against the sealing lip via the shoulder upon assembly of the housing, whereby the sealing lip completely surrounds a region of the membrane having the openings.

33. An aerosol therapy device according to claim 1, wherein the frame is coated with a soft resilient material.

34. An aerosol therapy device according to claim 33, wherein the coating of the frame is realized by way of direct insert molding in a two-component plastic injection molding process.

* * * * *